United States Patent
Im et al.

(10) Patent No.: US 6,418,795 B2
(45) Date of Patent: Jul. 16, 2002

(54) METHOD OF MEASURING SHEAR FRICTION FACTOR THROUGH BACKWARD EXTRUSION PROCESS

(75) Inventors: Yong Taek Im; Jae Seung Cheon; Soo Young Kim; Geun An Lee; Seong Hoon Kang, all of Taejon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/783,542

(22) Filed: Feb. 15, 2001

(30) Foreign Application Priority Data

Apr. 6, 2000 (KR) .......................................... 2000-17865

(51) Int. Cl.$^7$ ................................................. G01N 3/24
(52) U.S. Cl. ................................................. 73/841; 73/9
(58) Field of Search ............................... 73/9, 10, 841, 73/842

(56) References Cited

U.S. PATENT DOCUMENTS

| | | | |
|---|---|---|---|
| 4,240,290 A | * 12/1980 | Montoya et al. | 244/130 |
| 4,475,392 A | * 10/1984 | Ajagu et al. | 374/54 |
| 4,640,118 A | * 2/1987 | Kishida et al. | 73/9 |
| 5,107,448 A | 4/1992 | Nash | |
| 5,394,329 A | 2/1995 | Bridgens | |
| 5,628,230 A | * 5/1997 | Flam | 73/172 |
| 5,734,088 A | * 3/1998 | Gunderson | 73/9 |
| 5,736,630 A | 4/1998 | Welner | |
| 5,900,531 A | 5/1999 | Mani et al. | |
| 5,992,212 A | 11/1999 | Sims et al. | |

* cited by examiner

Primary Examiner—Max Noori
(74) Attorney, Agent, or Firm—Bacon & Thomas, PLLC

(57) ABSTRACT

A method of measuring shear friction factor between a workpiece material and a forming tool through a backward extrusion process. The method includes steps of: positioning the workpiece material at a groove previously manufactured on the forming die by turning; pressurizing the workpiece material to form an extruded product by pressure of a downwardly moving punch; forming tip on the extruded end of the extruded product; measuring an external diameter of the extruded product and a diameter of the tip, and obtaining a perpendicular distance by subtracting the diameter of the tip from the external diameter and dividing the subtracting result by two; and acquiring shear friction factor by calculating predetermined coefficients and a normalized perpendicular distance non-dimensionalized by thickness value of the extruded product. The thickness is defined as an interval between the external diameter of the extruded product and an external diameter of the punch.

8 Claims, 6 Drawing Sheets

METHOD OF MEASURING SHEAR FRICTION FACTOR THROUGH BACKWARD EXTRUSION PROCESS

BACKGROUND OF THE INVENTION

1. Field of the Invention

The present invention relates to a method of measuring the representative shear friction factor at the interface between a workpiece material and forming dies during bulk forming processes and, more particularly, to a method of more easily, effectively, and accurately measuring such representative shear friction factor through the backward extrusion process.

2. Description of the Prior Art

As well known to those skilled in the art, bulk forming processes have been typically and widely used for producing a variety of mechanical parts having different structures and operational functions. Particularly, such a bulk forming process can produce intermediate products having a shape and size similar to those of the desired final product, and so the bulk forming process reduces the number of operations for production and leads to material saving. In addition, bulk forming processes lead to good mechanical properties of the final products due to work hardening of the material during forming. In order to more effectively, or even optimally design such bulk forming processes, numerical analyses are frequently used while designing the process.

In order to use the numerical analysis in the design of a target bulk forming process effectively, it is necessary to accurately describe a variety of numerical parameters. Of such parameters to be estimated, the friction condition at the interface between the workpiece material and forming dies is very important since it directly influences both flow of the workpiece material and forming load during the target bulk forming process. In the end it will affect the success or failure of the process.

In order to express the friction condition quantitatively in bulk metal forming, a constant shear friction model is typically used in numerical analyses as expressed by the following equation (1).

$$\text{Frictional stress} = m_f \times \text{shear yield stress} \quad (1)$$

wherein, $m_f$: shear friction factor

In the above equation (1), the frictional stress is in proportion to the shear yield stress of the material, with the shear friction factor "$m_f$" determining the ratio of the proportional relationship. In general, this value is locally varying, depending on the surface quality, the type of lubrication, and the deformation condition at the interface.

Therefore, it is necessary to accurately measure the representative shear friction factor "$m_f$" as a single value in order to properly estimate the friction conditions in the target bulk forming process for simplicity and convenience for the process simulation.

A ring compression test has been most typically and widely used for measuring such shear friction factors.

In such ring compression test, variation in the inner diameter of an annular test specimen is measured during the compression of the test specimen to estimate the friction condition. This ring compression test is advantageous in that it is simple in its testing process. However, because this ring compression test is so exceedingly simple in its testing process, it may not be suitable for estimating the friction conditions in more complex bulk forming processes. In addition, the free surface generated during the ring compression test is quite small when compared with those of typical bulk forming processes. Another disadvantage of the ring compression test resides in that it is necessary to use nonlinear calibration curves to determine the desired shear friction factors. According to this method, since the shear friction factor is dependent on the deformation history, it is not easy to determine the representative constant shear friction factor.

Several methods of measuring shear friction factors that overcome the above-mentioned problems experienced in ring compression tests have been recently proposed and implemented. Of those recently proposed methods, various methods based on the backward extrusion process that is capable of generating a large amount of free surfaces have been preferred.

One such measuring method using the backward extrusion process predicts the shear friction factor by measuring the forming load during the process depending on the friction condition. However, this method of measuring the shear friction factor by measuring the difference in forming loads can be problematic in that the forming load has a direct connection with flow stress of the workpiece material, and thus it is necessary to accurately know flow stress of the material. Such a forming load can be considered only as an indirect measure of the friction condition.

Another method of measuring the shear friction factor based on a simultaneous forward and backward extrusion process has been proposed and used. This method is designed to determine the shear friction factor by measuring the ratio of material flow in the forward and backward ends in accordance with the friction condition. However, this measuring method is problematic in that it is insensitive at high levels of friction.

SUMMARY OF THE INVENTION

Accordingly, the present invention has been made with the aforementioned problems in mind. The objective of the present invention is to provide a method of measuring the representative constant shear friction factor at the interface between the workpiece material and forming dies during bulk forming processes through a backward extrusion process as a single value. This method can easily and effectively measure the constant shear friction factors for a variety of friction conditions and is suitable for estimating the friction condition of the complex bulk forming process.

In order to accomplish the above objective, the present invention uses a backward extrusion process, comprised of the following steps: positioning the workpiece material at a predetermined groove location within the forming die and pressurizing the workpiece material to form an extruded product with an apex formed on the backward extruded end; measuring the perpendicular distance "d" from the external side surface of the extruded product to the apex; and calculating the shear friction factor "$m_f$" using the measured perpendicular distance "d".

In the above measuring method, the workpiece material has a diameter equal to the average of the outer diameter of the punch and the inner diameter of the forming die, and is positioned such that its central axis is aligned with the central axes of both the punch and the forming die.

In addition, the representative shear friction factor "$m_f$", which has a range of 0.0~1.0, is calculated from the fact that the perpendicular distance "d" has a linear relationship with the shear friction factor "$m_f$".

Typically, numerical analyses are attractive for the design of bulk forming processes since they improve design efficiency, save both production time and material resources, and improve the quality of final products of the process. It is necessary to describe the friction condition properly and accurately in order to improve the reliability of numerical analyses of bulk forming processes. When the representative shear friction factor can be properly measured for the whole process as described above, it will be possible to select proper lubricants for target bulk forming processes.

Proper lubrication in bulk forming processes can lead to reduction of forming loads, extension of die life, and reduction of energy consumption. Also, such an efficient and accurate measurement of friction conditions can aid the development of environment friendly lubricants for general use in bulk forming processes.

BRIEF DESCRIPTION OF THE DRAWINGS

The objectives, features, and other advantages of the present invention will be more clearly understood from the following detailed description given in conjunction with the accompanying drawings, in which.

DETAILED DESCRIPTION OF THE INVENTION

Figure 1:
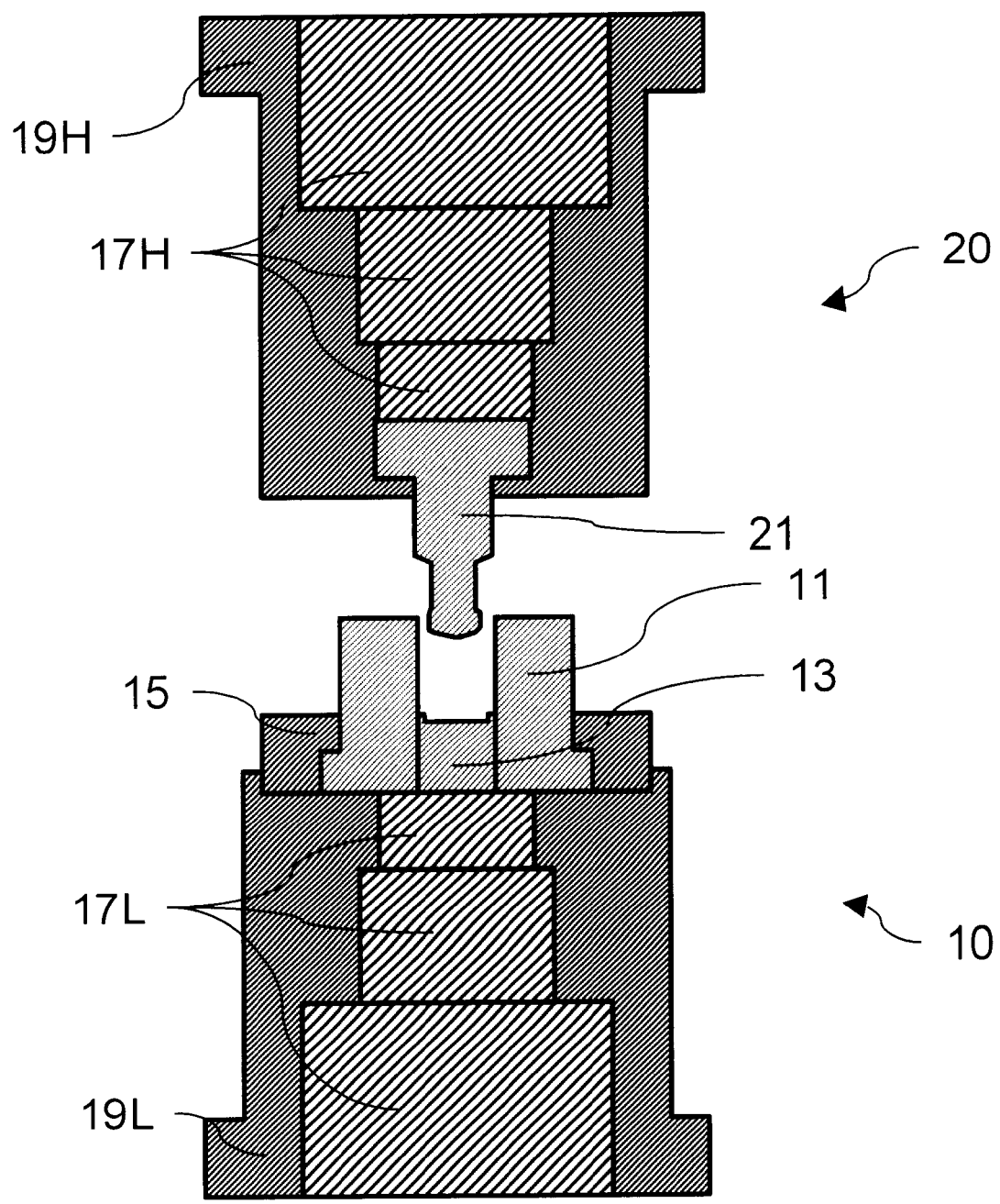
FIG. 1 is a sectional view of the backward extrusion tool set-up designed to perform the backward extrusion process in accordance with the preferred embodiment of the present invention.
Figure 2:
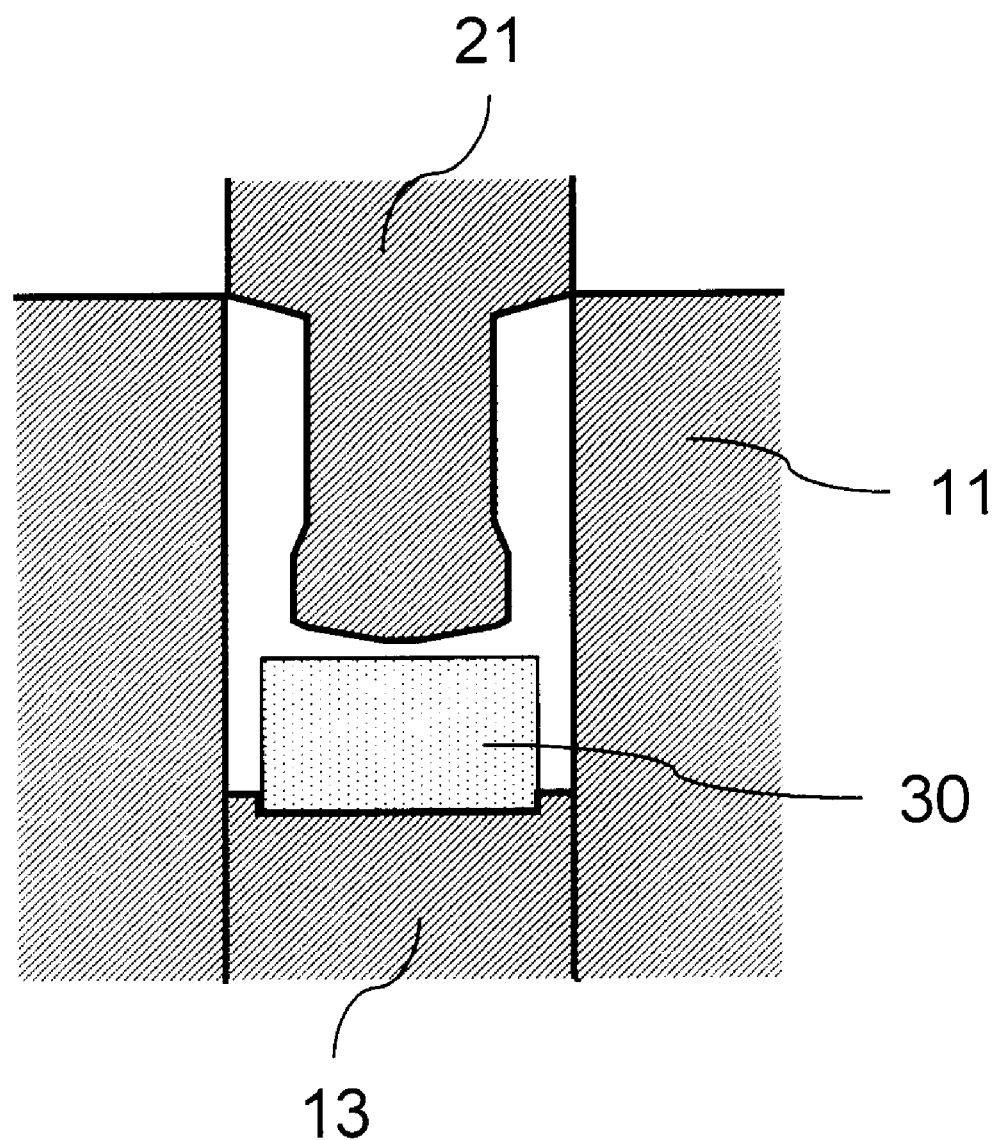
FIG. 2 is a sectional view showing the position of a workpiece material within the backward extrusion tool set-up of FIG. 1.
Figure 4:
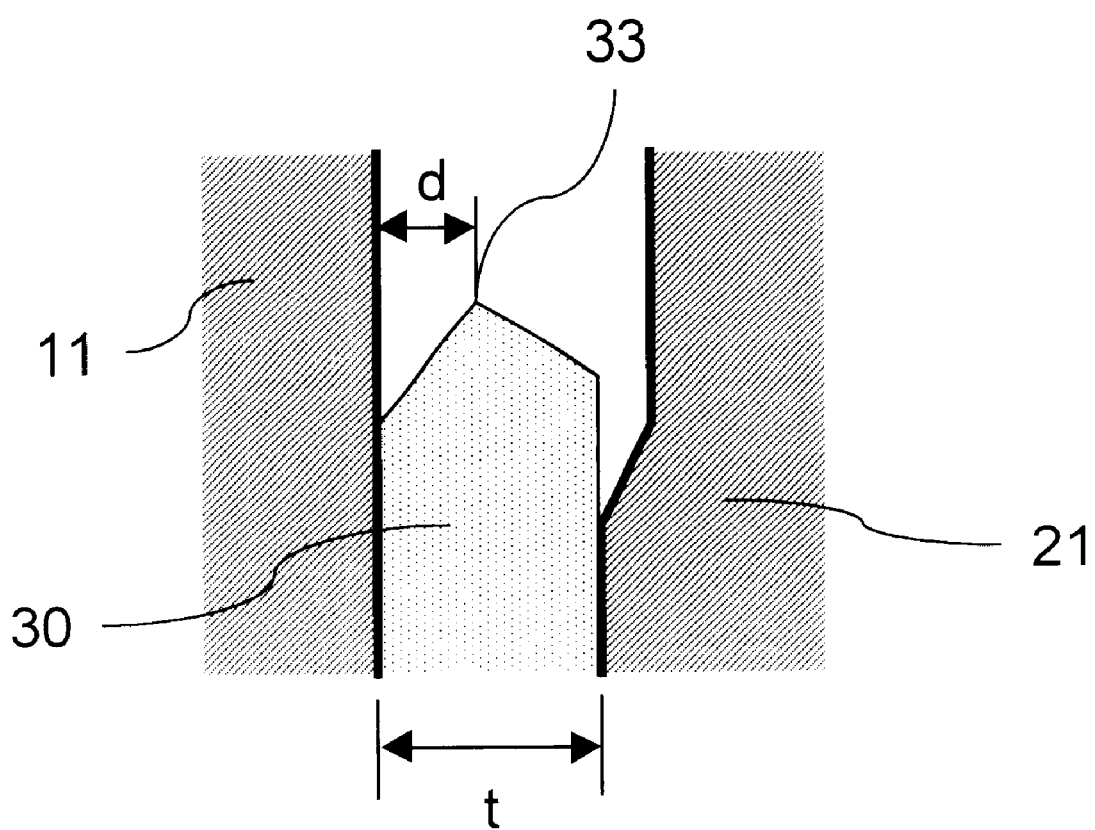
FIG. 4 is a sectional view showing the apex of an extruded product formed by the backward extrusion process of FIGS. 3a to 3d and the perpendicular distance "d" to this apex from the external side surface of the extruded product along with the thickness "t" of the extruded end.
Figure 5:
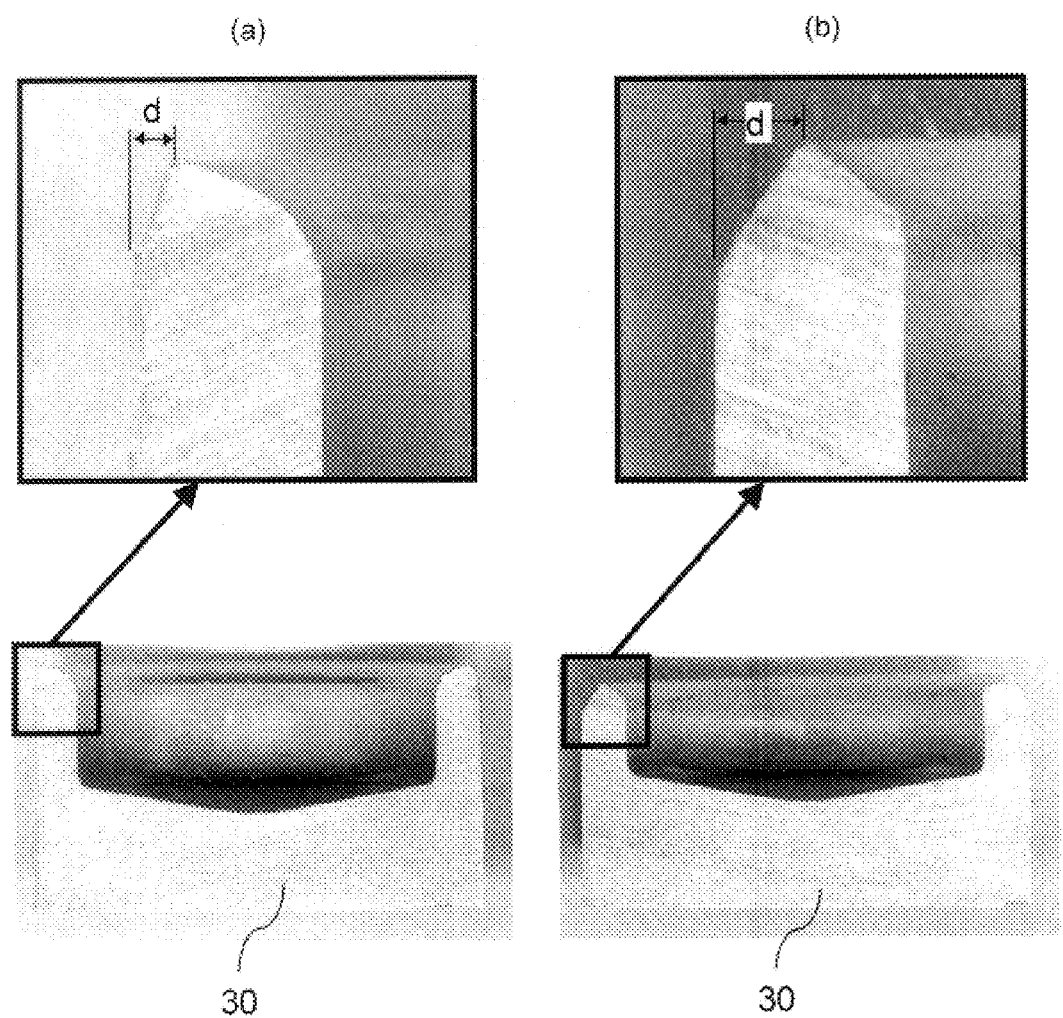
FIGS. 5a and 5b are experimental results showing the apexes of extruded products from this invention, with the position of the apexes changing in accordance with lubrication conditions during the backward extrusion process of FIGS. 3a to 3d.
Figure 6:
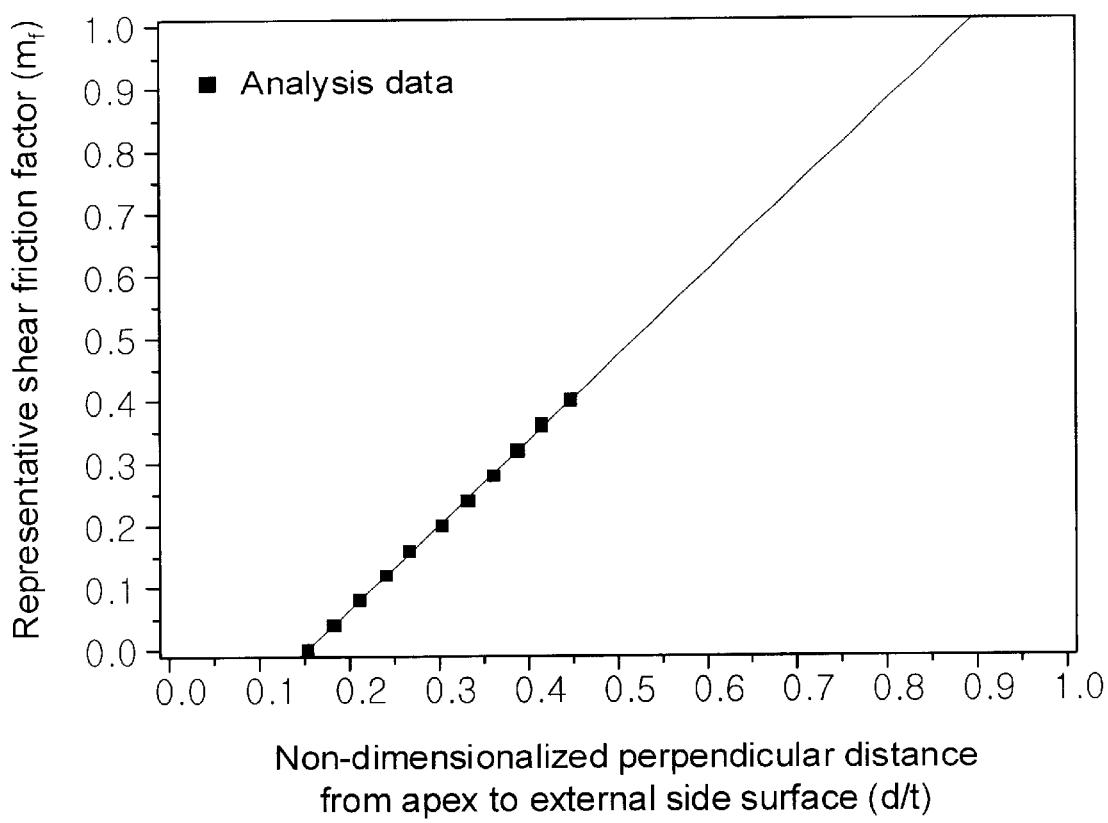
FIG. 6 is a graph showing the linear relationship between shear friction factor "$m_f$" and "d/t", where "d" is the perpendicular distances from the apex to the external side surface of the extruded product and "t" is the thickness of the extruded end.

FIG. 1 is a sectional view of the backward extrusion tool set-up designed to perform the backward extrusion process in accordance with the preferred embodiment of the present invention. FIG. 2 is a sectional view showing the position of a workpiece material within the backward extrusion tool set-up of FIG. 1. FIGS. 3a to 3d are sectional views showing the four stages of the backward extrusion process performed to measure the representative shear friction factor in accordance with the present invention. FIG. 4 is a sectional view showing the apex of an extruded product formed by the backward extrusion process of FIGS. 3a to 3d and the perpendicular distance "d" to this apex from the external side surface of the extruded product along with the thickness "t" of the extruded end. FIGS. 5a and 5b are experimental results showing the apexes of extruded products from this invention, with the position of the apexes changing in accordance with lubrication conditions during the backward extrusion process of FIGS. 3a to 3d. FIG. 6 is a graph showing the linear relationship between the shear friction factor "$m_f$" and "d/t", where "d" is the perpendicular distances from the apex to the external side surface of the extruded product and "t" is the thickness of the extruded end.

As shown in FIG. 1, the backward-extruding tool set-up, designed to perform the backward extrusion process in accordance with the preferred embodiment of this invention, comprises two parts: a die part 10 and a punch part 20. The punch part 20, which moves vertically with the movement of the upper press, contains the punch 21 that is used for applying extrusion force to a workpiece material 30. The die part 10 supports the workpiece material 30 when the material 30 within the die part 10 is pressed down by the punch 21.

The above die part 10 comprises an external die 11, a lower die 13, a die mounting flange 15 and a lower die housing 19L. The external die 11 has a hollow cylindrical shape provided with a central opening for receiving the vertically movable punch 21 therein, while the lower die 13 is firmly positioned at the bottom of the central opening of the external die 11. The lower die 13 with a groove at the center thus creates the forming die of the tool-set in cooperation with the external die 11. The annular die-mounting flange 15 is firmly set around the external die 11, thus holding the external die 11 in place. The lower die housing 19L is positioned under and supports the external die 11, the lower die 13 and the die-mounting flange 15. Hydrostatic pressure pads 17L are set within the lower die housing 19L.

The punch 21 of the punch part 20 can freely move into and out of the central opening of the external die 11 of the die part 10. An upper die housing 19H surrounds the upper portion of the punch 21, with hydrostatic pressure pads 17H set within the cavity of the upper die housing 19H.

As shown in FIG. 2, the workpiece material 30 is positioned on the groove of the top surface of the lower die 13. This workpiece material 30 has a cylindrical shape, with the diameter of the workpiece material 30 set as the average of the outer diameter of the punch 21 and the inner diameter of the external die 11. During the backward extrusion process, the above workpiece material 30 must be positioned on the top groove of the surface of the lower die 13 such that the central axis of the material 30 is precisely aligned with the central axes of both the punch 21 and the external die 11. After the workpiece material 30 is properly positioned on the top groove of the surface of the lower die 13 within the external die 11, the punch 21 is moved downward to apply the required extrusion pressure to the material 30.

Figure 3:
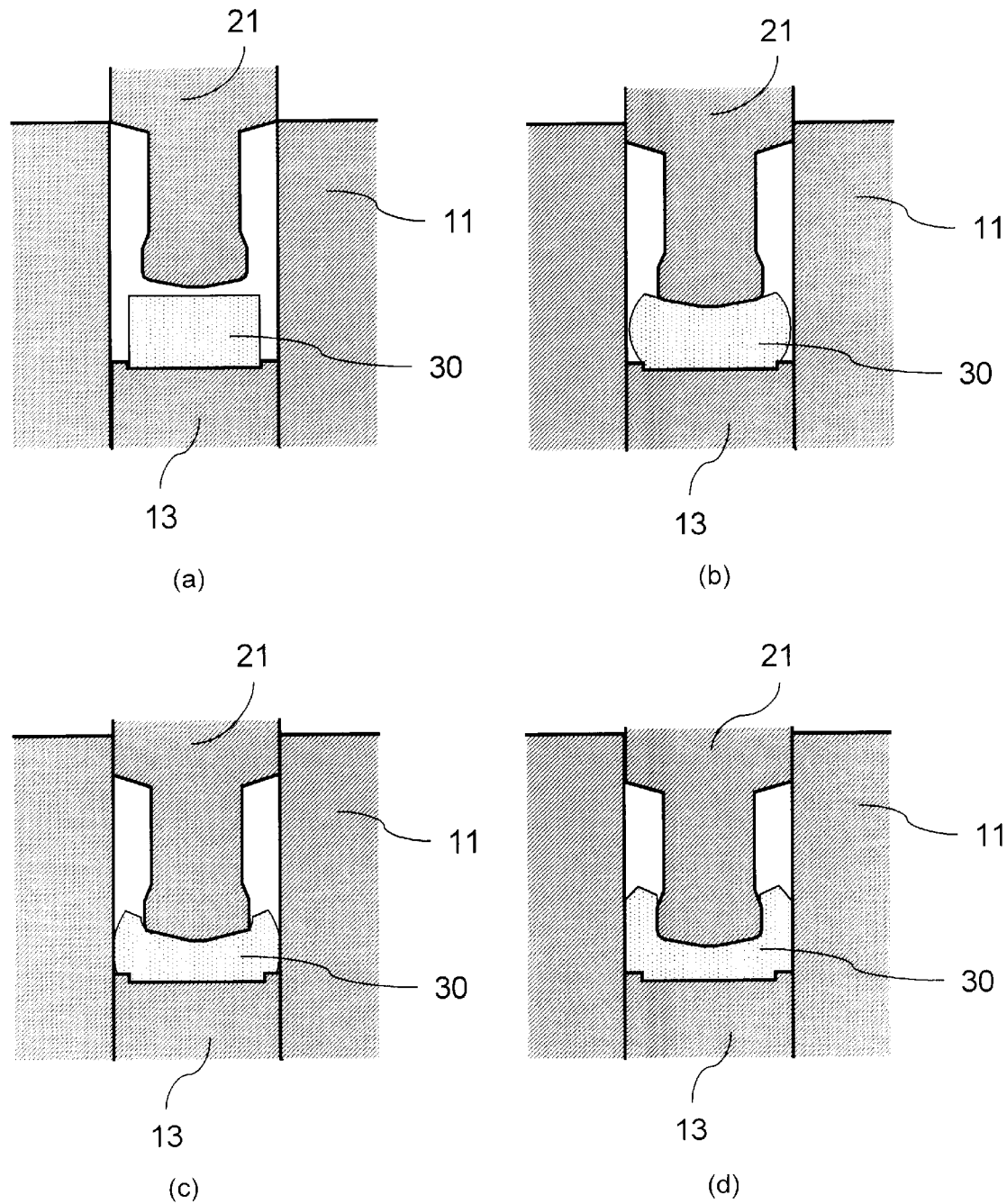
FIGS. 3a to 3d are sectional views showing the four stages of the backward extrusion process performed to measure the shear friction factor in accordance with the present invention.

When the punch 21 is moved downward applying extrusion pressure on the workpiece material 30, the material 30 deforms as shown in FIGS. 3a to 3d. The extruded product is formed to have a shape defined by the external shape of the punch 21, internal shape of the external die 11, and top surface of the lower die 13. Such a backward extrusion process can be described in more detail with reference to FIGS. 3a to 3d as follows. FIG. 3a shows the initial non-pressure position, wherein the punch 21 does not apply any extrusion pressure to the material 30. FIG. 3b shows the barreling position, wherein the punch 21 applies the pressure to the material 30 such that barreling of the material 30 occurs. FIG. 3c shows the initial apex forming position, wherein the continuously applied pressure by the punch 21 forms the apex 33 on the material 30. FIG. 3d shows the final apex position, wherein the formation of the apex 33 on the material 30 is completed.

As shown in FIG. 4, the extruded end of the completely processed material 30 has a cross-section similar to a triangle, with the top apex 33 of the extruded end being positioned at a certain perpendicular distance "d" from the external side surface of the workpiece 30. The thickness of the extruded end of the workpiece 30 is represented by "t".

The above perpendicular distance "d" between the top apex 33 of the extruded end and the external side surface of the workpiece 30 is the value that can be used as an effective measure of the representative shear friction factor. The characteristics of the perpendicular distance "d" are described in detail herein below with reference to FIGS. 5a and 5b.

In the experimental backward extrusion results of FIGS. 5a and 5b for measuring the characteristics of the perpendicular distance "d", an aluminum alloy, 6061-O, was used as the workpiece material 30.

FIG. 5a shows the apex 33 of the material 30 when the material 30 was backward extruded under a low lubrication condition, free of any lubricant. FIG. 5b shows the apex 33 of the material 30 when the material 30 was backward extruded under a high lubrication condition using a proper lubricant, namely, a mixture of grease and $MOS_2$. The perpendicular distance "d" of the embodiment of FIG. 5a is about 1.65 mm, while the perpendicular distance "d" in the embodiment of FIG. 5b is about 0.75 mm. It is thus noted that the perpendicular distance "d" is related inversely to the lubrication condition of the backward extrusion process. That is, the high lubrication condition results in a short perpendicular distance "d", while the low lubrication condition results in a long perpendicular distance "d". Particularly, the perpendicular distance "d" increases linearly in proportion to increases in the representative shear friction factor. Such experimental results were confirmed from analyses using an analysis program based on the rigid-viscoplastic finite element method that is widely used in the numerical analysis of bulk forming processes.

FIG. 6 is a graph showing the linear relationship between the representative shear friction factors "$m_f$" and the perpendicular distance "d", which is non-dimensionalized by the thickness "t" of the extruded end of the workpiece 30. Since the thickness "t" of the extruded products is 3.4 mm, "d/t" for the embodiment of FIG. 5a can be calculated to be 0.49, while it is 0.22 for the embodiment of FIG. 5b. This linear relationship is expressed by the following equation (2).

$$\text{Representative shear friction factor } (m_f) = 1.36 \times d/t - 0.21 \quad (2)$$

As expressed in the above equation (2), it is possible to simply and easily measure the representative shear friction factor using the geometrical characteristics of the extruded product. By using equation (2), the representative shear friction factor for the embodiment of FIG. 5a extruded under low lubrication condition can be calculated to be about 0.46, while the representative shear friction factor for the embodiment of FIG. 5b extruded under high lubrication condition can be calculated as 0.09.

As described above, the present invention based on backward extrusion provides a method of measuring the representative shear friction factor at the interface between a workpiece material and forming dies during bulk forming processes. The measuring method is very simple and suitable for estimating the friction conditions of complex bulk forming processes as a single value.

In addition, it is possible to estimate friction conditions for a large range of representative shear friction factors ($m_f = 0.0 \sim 1.0$), and so the appropriate constant shear friction factors for a variety of lubrication conditions are easily measured. This measuring method thus improves both the reliability of numerical analyses and the design efficiency of bulk forming processes to improve the final quality of bulk forming products.

In the above description, the preferred embodiment of the present invention for measuring the representative shear friction factor using backward extrusion has been described for illustrative purposes. That is, the method according to the preferred embodiment of this invention is designed to measure the representative shear friction factor through a backward extrusion process as a single value. However, it should be understood that the present invention is not limited to the above-mentioned embodiment and those skilled in the art will appreciate that various modifications, additions and substitutions are possible, without departing from the scope and spirit of the invention as disclosed in the accompanying claims.

What is claimed is:

1. A method of measuring shear friction factor between a workpiece material and a forming tool through a backward extrusion process, comprising the steps of:

positioning said workpiece material at a groove previously manufactured on the forming die by turning;

pressurizing the workpiece material to form an extruded product by pressure of a downwardly moving punch;

forming an annular tip on the extruded end of said extruded product;

measuring an external diameter of said extruded product and a diameter of the annular tip, and obtaining a perpendicular distance between the annular tip and the external diameter of said extruded product by subtracting the diameter of the annular tip from the external diameter and dividing the subtraction result by two; and acquiring shear friction factor by calculating predetermined coefficients and a normalized perpendicular distance non-dimensionalized by thickness value of the extruded product, the thickness being defined as an interval between the external diameter of said extruded product and an external diameter of the punch.

2. The method according to claim 1, wherein a diameter of said initial workpiece material is determined as an average value of an outer diameter of said punch and inner diameter of the forming die.

3. The method according to claim 1, wherein said shear friction factor is calculated by a linearity between the shear friction factor and the perpendicular distance.

4. The method according to claim 1, wherein the outer diameter of the extruded product is equal to the inner diameter of the forming die.

5. The method according to claim 1, wherein the diameter of the groove on the forming die is equal to that of the initial workpiece material.

6. The method according to claim 1, further comprising the step of providing lubrication between outer surfaces of the workpiece material and the punch and inner surface of the forming die.

7. The method according to claim 6, wherein said perpendicular distance between the annular tip and the external diameter of said extruded product is directly related to application of lubricant.

8. The method according to claim 1, wherein said workpiece material comprises a cylindrical shape.

* * * * *